United States Patent [19]
Blair

[11] Patent Number: 5,989,184
[45] Date of Patent: Nov. 23, 1999

[54] APPARATUS AND METHOD FOR DIGITAL PHOTOGRAPHY USEFUL IN CERVICAL CANCER DETECTION

[75] Inventor: Kerry L. Blair, Overland Park, Kans.

[73] Assignee: Medtech Research Corporation, Lenexa, Kans.

[21] Appl. No.: 08/985,642

[22] Filed: Dec. 5, 1997

Related U.S. Application Data

[63] Continuation-in-part of application No. 08/832,802, Apr. 4, 1997, which is a continuation of application No. 08/832,944, Apr. 4, 1997.

[51] Int. Cl.$^6$ ........................................................ A61B 1/05
[52] U.S. Cl. ........................................... 600/167; 600/109
[58] Field of Search .................................. 600/102, 166, 600/167, 109

[56] References Cited

U.S. PATENT DOCUMENTS

| | | |
|---|---|---|
| 3,805,596 | 4/1974 | Klahr . |
| 4,300,570 | 11/1981 | Stafl . |
| 4,407,290 | 10/1983 | Wilber . |
| 4,488,039 | 12/1984 | Sato et al. ............................... 600/167 |
| 4,519,684 | 5/1985 | Francis, Jr. et al. . |
| 4,588,294 | 5/1986 | Siegmund . |
| 4,590,923 | 5/1986 | Watanabe ............................... 600/102 |
| 4,841,555 | 6/1989 | Doi et al. . |
| 4,860,371 | 8/1989 | Matsuyama et al. . |
| 4,862,873 | 9/1989 | Yajima et al. ........................... 600/166 |
| 4,888,490 | 12/1989 | Bass et al. . |
| 4,905,670 | 3/1990 | Adair . |
| 5,026,368 | 6/1991 | Adair . |
| 5,036,853 | 8/1991 | Jeffcoat et al. . |
| 5,046,935 | 9/1991 | Kikuchi .................................. 600/109 |
| 5,179,938 | 1/1993 | Lonky . |
| 5,211,938 | 5/1993 | Kennedy et al. . |
| 5,214,456 | 5/1993 | Gersten . |

(List continued on next page.)

OTHER PUBLICATIONS

Paola M. Cristoforoni, M.D., "Computerized Colposcopy Results of a Pilot Study and Analysis of Its Clinical Relevances", *Obstetrics & Gynecology;* vol. 85, No. 6, Jun. 1995, pp. 1011–1016.

L. Stewart Massad, "Use of Speculoscopy in the Evaluation of Women with Atypical Papanicolaou Smears", *The Journal of Reproductive Medicine,* vol. 38, No. 3, Mar. 1993, pp. 163–169.

W. Mann, "Papanicolaou Smear Screening Augmented by a Magnified Chemiluminescent Exam", *International Federation of Gynecology and Obstetrics,* vol. 43, 1993, pp. 289–296.

W.P. Soutter, "Computerization of a Colposcopy Clinic", *British Journal of Obstetrics and Gynecology,* vol. 98, Aug. 1991, pp. 824–828.

William E. Crisp, M.D., "The Computerized Digital Imaging Colposcope: Future Directions", *American Journal of Obstetrics and Gynecology,* vol. 162, No. 6, Jun. 1990, pp. 1491–1498.

Vittorio Contini, "Colposcopy and Computer Graphics: A New Method?", *American Journal of Obstetrics and Gynecology,* vol. 160, No. 3, Mar. 1989, pp. 535–538.

*Colposcopes & Accessories,* Leisegang Medical Inc.
*Applying Digital Processing Methods in the Analysis of Refinal Structure,* Sunanda Mitra.
*How Computer Displays Work,* Computer Display Systems.
*Applied Image Processing,* pp. 32–56.

Primary Examiner—Paul J. Hirsch
Attorney, Agent, or Firm—Lathrop & Gage LC

[57] ABSTRACT

An apparatus for digital colposcopy and videography comprises a digital imaging camera that is operably coupled to the optical path of the digital colposcope by means of a beam splitter so that a digital image of the cervico-vaginal tissue can be captured. The digital imaging camera and digital colposcope are mounted to one end of an articulating arm of the apparatus. A digital processing means is operably connected to the digital imaging camera to create a digital image. The digital processing means is housed in a stand of the assembly.

9 Claims, 11 Drawing Sheets

U.S. PATENT DOCUMENTS

| | | | |
|---|---|---|---|
| 5,251,613 | 10/1993 | Adair | 600/102 |
| 5,309,214 | 5/1994 | Hashimoto . | |
| 5,329,938 | 7/1994 | Lonky . | |
| 5,368,015 | 11/1994 | Wilk | 600/166 |
| 5,413,108 | 5/1995 | Alfano . | |
| 5,421,339 | 6/1995 | Ramanujam et al. . | |
| 5,441,042 | 8/1995 | Putman | 600/102 |
| 5,450,857 | 9/1995 | Garfield . | |
| 5,496,261 | 3/1996 | Sander | 600/102 |
| 5,522,789 | 6/1996 | Takahashi | 600/166 |
| 5,554,160 | 9/1996 | Caillouette . | |
| 5,603,687 | 2/1997 | Hori et al. | 600/166 |

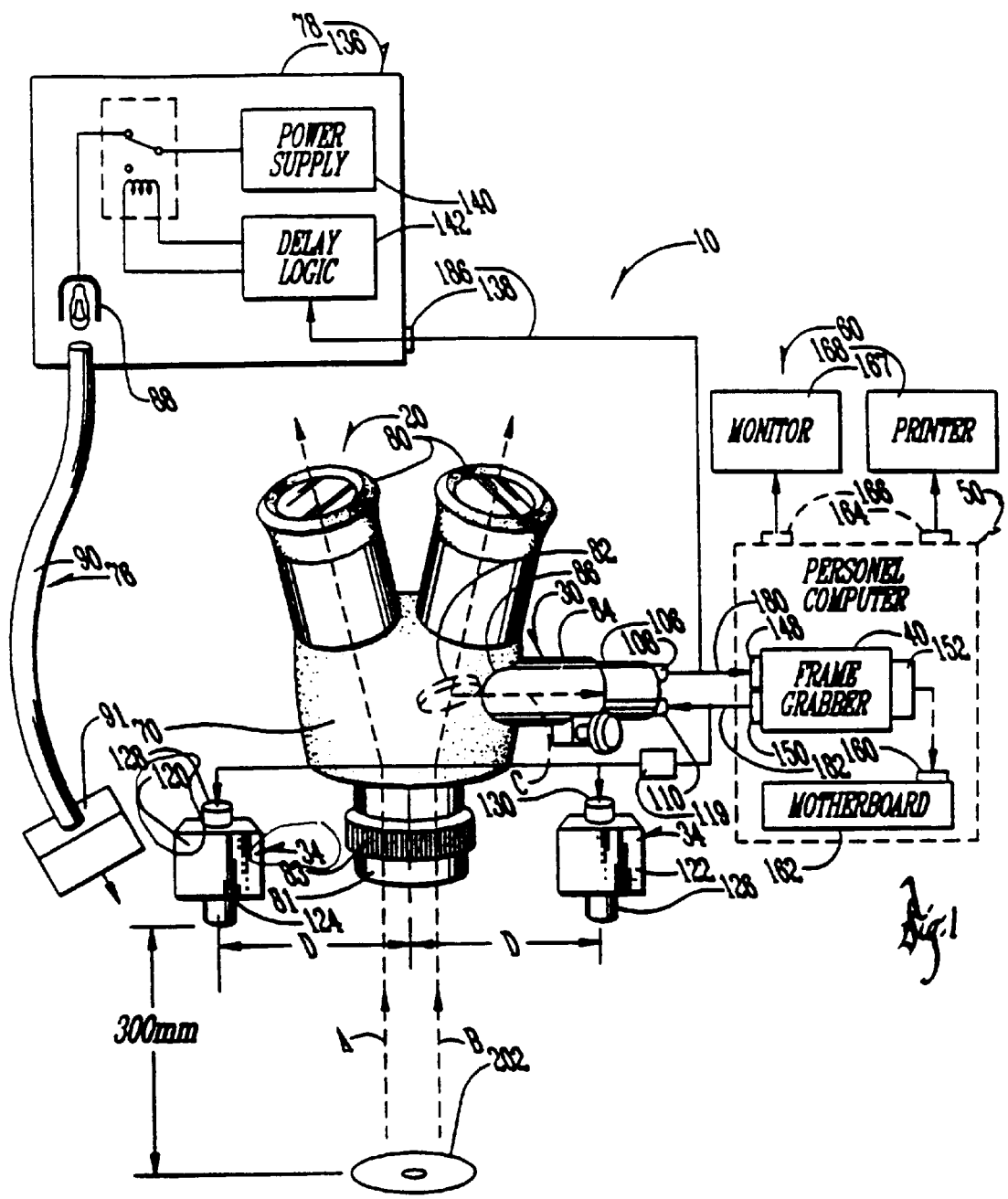

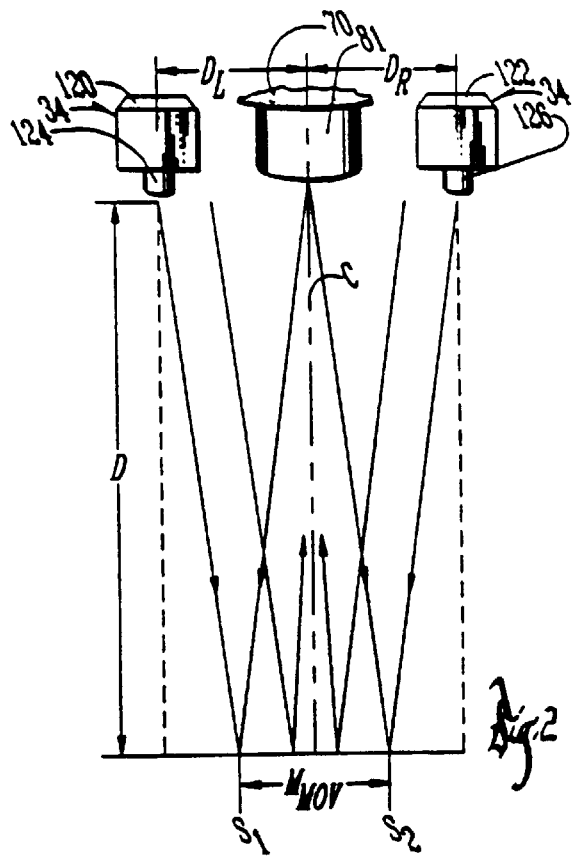
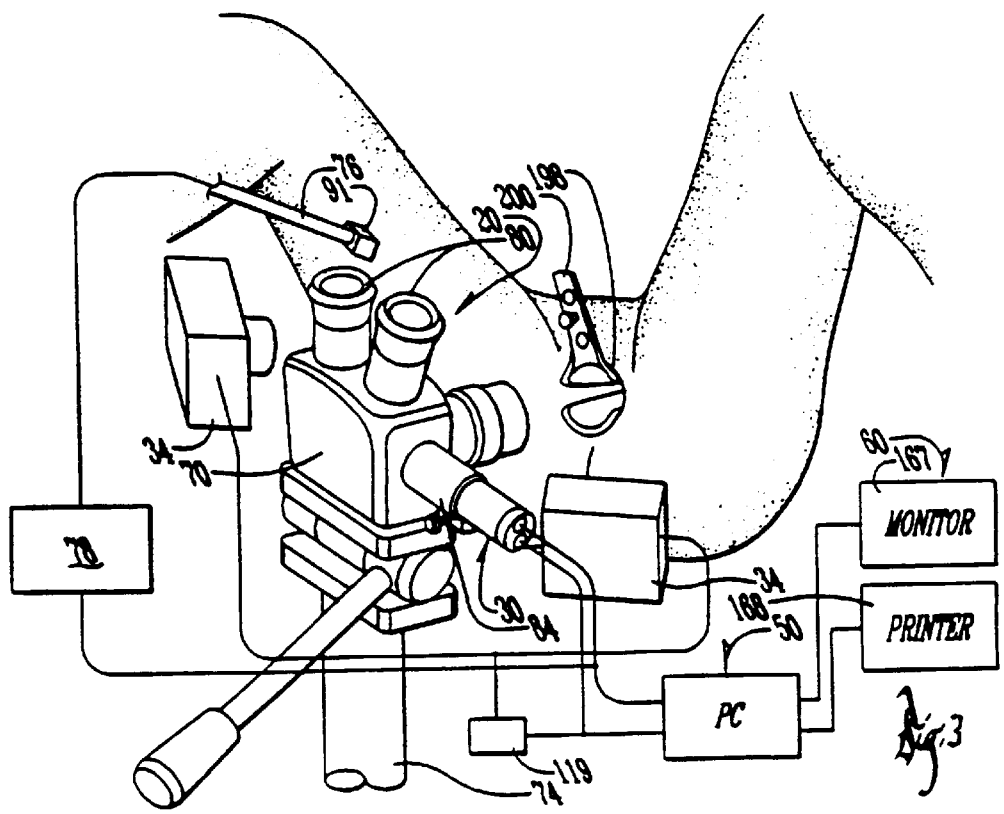

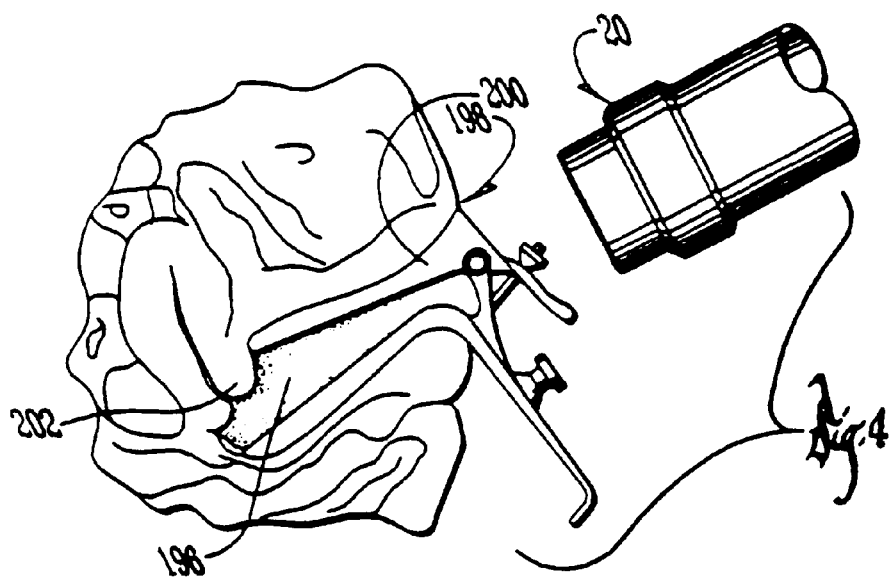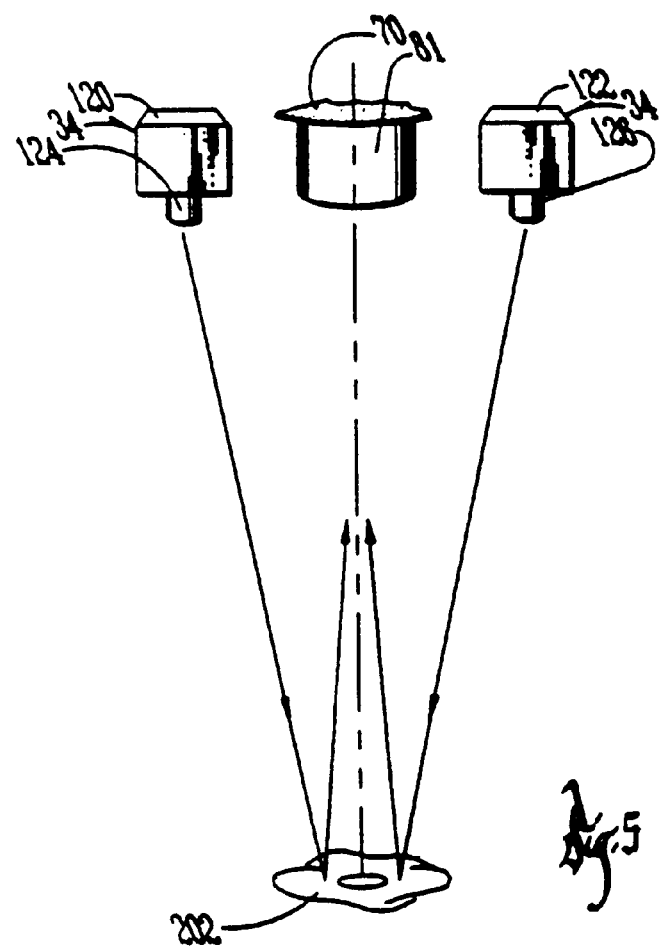

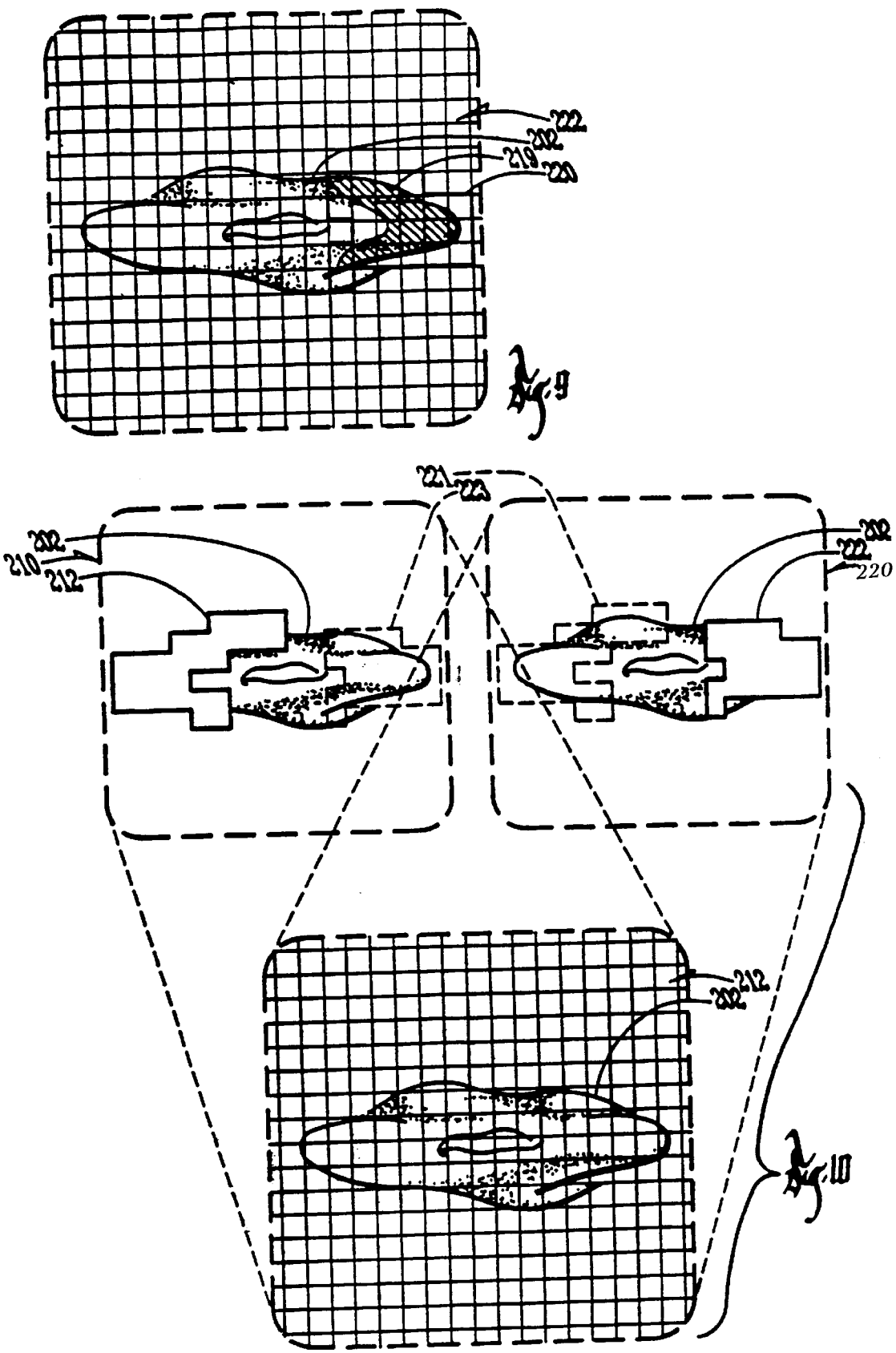

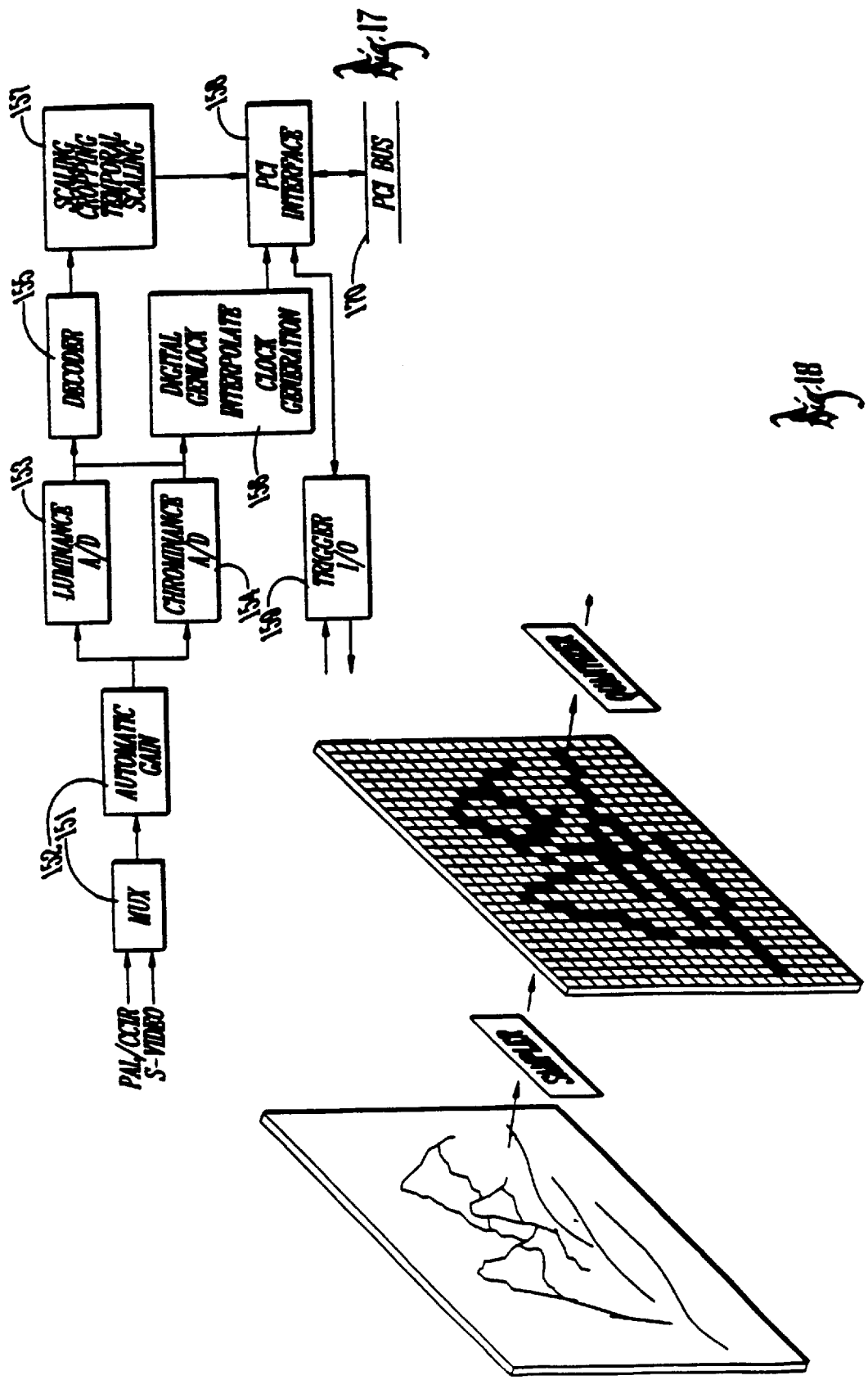

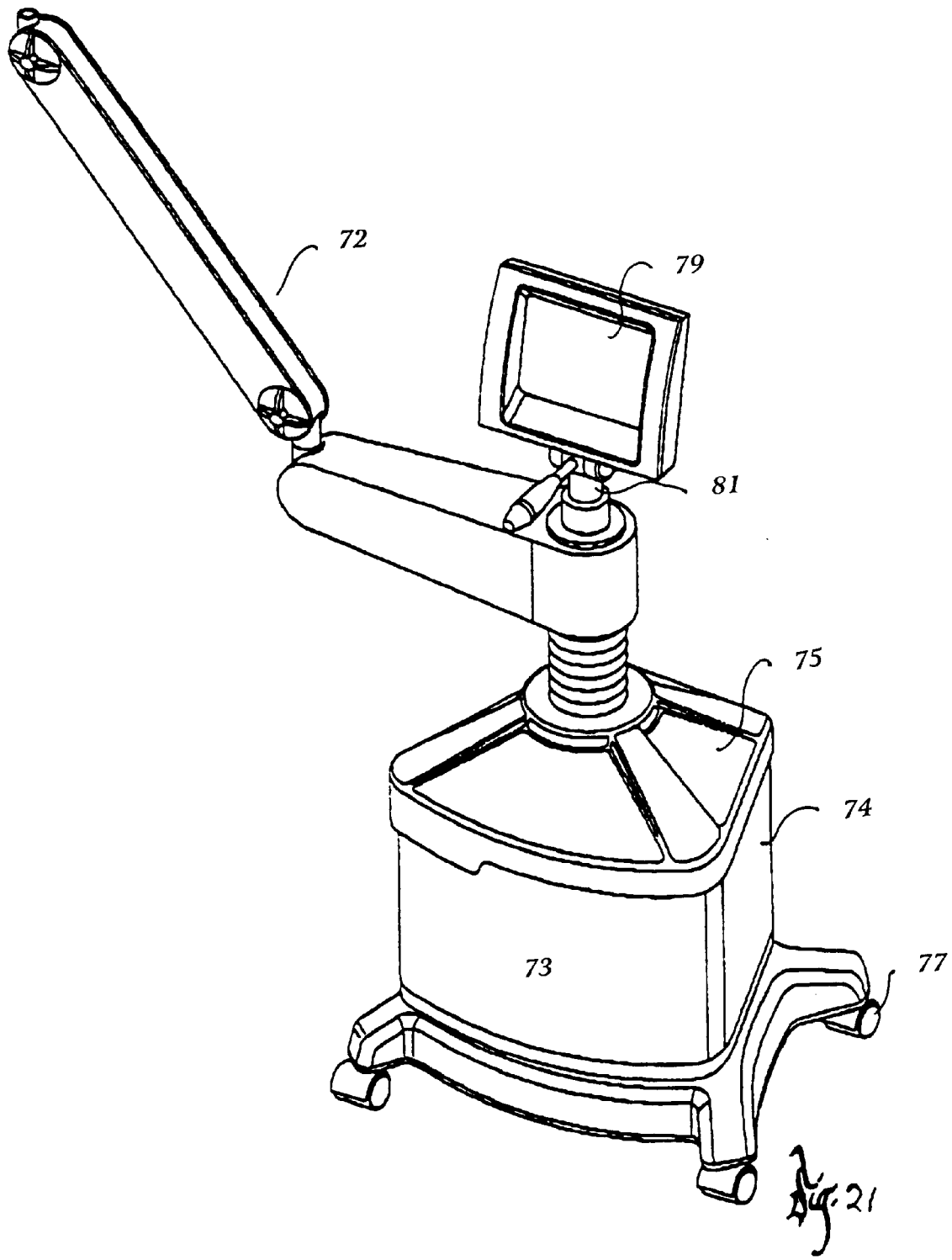

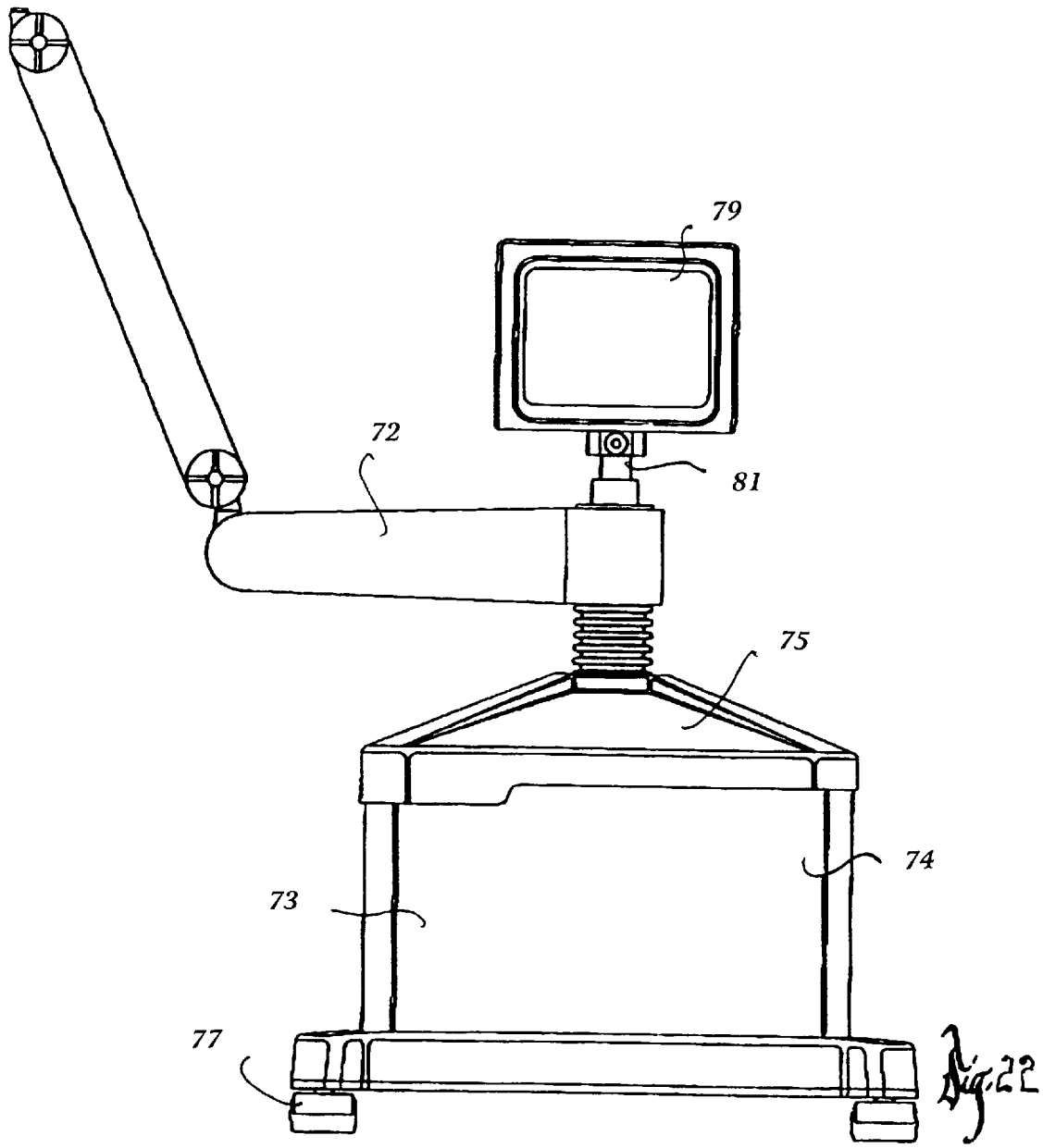

APPARATUS AND METHOD FOR DIGITAL PHOTOGRAPHY USEFUL IN CERVICAL CANCER DETECTION

1. CROSS-REFERENCE TO RELATED APPLICATION

The present invention is a continuation-in-part of co-pending application Ser. No. 08/832,802 filed on Apr. 4, 1997 which is a continuation of application Ser. No. 08/832,944 filed on Apr. 4, 1997.

1.0 BACKGROUND OF THE INVENTION

1.1. FIELD OF THE INVENTION

The present invention relates generally to the detection of cervical cancer. More particularly, the present invention relates to an apparatus method for the visual examination of cervical epithelium or other cervico-vaginal tissue by means of a colposcopy assembly capable of producing a digital images of cervico-vaginal tissue.

1.2. PROBLEMS IN THE ART

1.2.1 General Setting of the Invention

Over the last fifty years, Papanicolaou Smear ("Pap Smear") has become the cornerstone of efforts to reduce cervical cancer mortality. Pap Smear is effective because it identifies the latest stages of cervical cancer. Current estimates are that 60–70 million Pap Smears are done in the U.S. each year. Pap Smear has, thus, become a norm in the detection of cervical cancer. In spite of its broad acceptance in the medical community, studies indicate that Pap Smear screenings will fail to detect from 50%–80% of low grade cancerous lesions, and even 15%–30% of high grade cancerous lesions.

1.2.2 Conventional Methods and Systems

When conducting Pap Smear screenings, the gynecologist collects exfoliated cells from the surface of the cervix and places them on slides that are sent to cytologists for further examination. Cytologists then review the cells placed on the slides and look for abnormal cells. If abnormal cells are found, the Pap Smear is considered to be positive. If no abnormal cells are found, the Pap Smear is considered to be negative. It is also possible that Pap Smear slides cannot be properly evaluated by the cytologist because of technical problems associated with the Pap Smear collection process such inadequate cell count, improper slide fixation, etc.

In the early stages of cervical disease, abnormal cell exfoliation is slow and most abnormal cells are located below the surface or are trapped by a keratin barrier covering the cervical surface. In these circumstances, the Pap Smear screening process is a relatively insensitive indicator of cervical health due to inaccessibility of abnormal cells that are otherwise indicators of cancerous or pre-cancerous tissue. Human Papilloma Virus ("HPV") is the most common cause of keratin barriers to exfoliation. Further, it is commonly known that a significant portion of the U.S. population harbors this virus which therefore, complicates the challenge of cervical cancer detection when using the Pap Smear as the principal screening procedure.

Because of a variety of problems associated with Pap Smear screening, it is well known that the Pap Smear procedure has both a high false negative, and a high false positive rate. Nevertheless, in spite of its cancer detection shortcomings, Pap Smear screening is generally recognized as a practical and economical procedure for the early detection of cervical cancer. While the Pap Smear process is designed for initial screening, colposcopy and related procedures are generally used to confirm Pap Smear abnormalities and to grade cancerous and potential cancerous lesions.

Since its introduction in 1925, colposcopy has acquired wide recognition as a follow-up clinical procedure for patients identified by Pap Smear screening as having possible cervical abnormalities. It is generally recognized that colposcopy is highly effective in evaluating patients with abnormal Pap Smears and has therefore become the standard of medical care in the Western world for this circumstance. It is estimated that approximately 4 million colposcopy examinations are currently performed in the U.S. each year. Its routine use, however, is time consuming and costly. Further, proper colposcopy examinations are limited by the expertise of the examiner.

The recent emergence of computer-aided colposcopy creates a potential for the enhancement of colposcopic assessments. Computer-aided colposcopy provides for expanded utility in digital colposcopic photography and videography, and in the management of information generated by the colposcopic examination, including computer-aided processing and enhancement of colposcopic-generated images. Computer-aided colposcopy also sets up a platform that will facilitate the emergence and development of "telemedicine" by permitting the communication of diagnostic digital image information across tele-communication networks.

1.2.3 Shortcomings-Needs

Colposcopy, however, is faced with its own set of challenges. It is a subjective assessment and the quality depends greatly on the expertise of the practitioner. It is time consuming with significant legal risks associated with false negative evaluations, and is therefore expensive. Computer-aided colposcopy, while capable of generating, storing and manipulating image data for the production of high-quality images, is unwieldy and expensive. These colposcopes send signals to a remote computer through 5 to 7 meter long coaxial cables. As the colposcope is maneuvered to visualize the cervix, the wiring may become tangled with the patient or other equipment. Further, the remote location of the computer and video monitor prevents the patient from viewing the image as the examination is being conducted. Thus, these colposcopes provide an uncomfortable setting for the patient during examination. Further, the remote location of the video monitor also makes the viewing of the image difficult for the doctor while operating the colposcope.

A need, therefore, exists in the area of cervical cancer screening and detection for a simple, low-cost colposcope assembly for use in conjunction with the Pap Smear procedure that would improve the overall statistical accuracy of the screening effort. The traditional colposcopy should be made easier to perform by integrating the computer with the colposcope assembly to reduce patient discomfort and enable the doctor to view the video monitor and determine the quality of the image without leaving the colposcope.

1.3. OBJECTS, FEATURES AND ADVANTAGES OF THE INVENTION

In accordance with the present invention, a method and apparatus are disclosed for digital colposcopic photography and videography. The present invention enables real-time imaging and archiving of images of the entire cervix for the purpose of detecting cancerous and pre-cancerous tissue.

Thus, an object of the present invention is to provide a computer-aided colposcopy device, a so-called "digital colposcope," having non-invasive, digital camera capability that provides for image enhancement, documentation, and an image archival means.

Another object of the invention is to physically mount the computer display in on the colposcope assembly in a fashion that would allow the patient to view the digital photographic colposcopic image so that the doctor might better educate the patient as to the medical conditions of the colposcopic view.

Another object of the invention is to employ digital photographic techniques with the computer processing and display technology in order to provide relatively instantaneous presentation of the digital photographic image on a color computer display. Such display and computer being an integral part of the digital colposcope. This rapid feedback of image quality would allow a doctor to re-take any digital photographic images that were deemed unsatisfactory.

Another object of the invention is to provide a wireless computer interface capability between the digital colposcope and a computerized digital image archival system.

Another object of the invention is to provide such a digital colposcope with improved screening and diagnostic capability, which is useful to grade lesion.

2. SUMMARY OF THE INVENTION

These and other objects of the invention are attained by the present invention. According to the invention, an apparatus for digital colposcopy and videography is provided that comprises a digital imaging camera that is operably coupled to the optical path of the digital colposcope by means of a beam splitter so that a digital image of the cervix can be captured. The digital imaging camera and digital colposcope are mounted to one end of an articulating arm of the apparatus. A digital processing means is housed in a stand of the assembly and is operable to create a digital image.

3. BRIEF DESCRIPTION OF THE DRAWINGS

FIG. 1 is a diagram of an exemplary system designed in accordance with the present invention;

FIG. 2 is a diagram illustrating the optical path of the colposcopic and the strobe light assembly;

FIG. 3 is a perspective view of the apparatus of the present invention positioned for taking a photograph of the cervix;

FIG. 4 is a schematic view, partially in cross-section, of the vaginal area showing the optical path of the inventive apparatus;

FIG. 5 is a schematic diagram of the apparatus photographing a cervix;

FIGS. 6–11 are representations of cervix images produced by the apparatus;

FIG. 17 is a block diagram of a PIXCI imaging board;

FIG. 18 is a representation of a digitalization process;

FIG. 21 is a perspective view of a stand and extension arm of the present invention, and FIG. 22 is a side elevational view of a stand and extension arm of the present invention.

4. DETAILED DESCRIPTION OF THE PREFERRED EMBODIMENT

Figure 6:
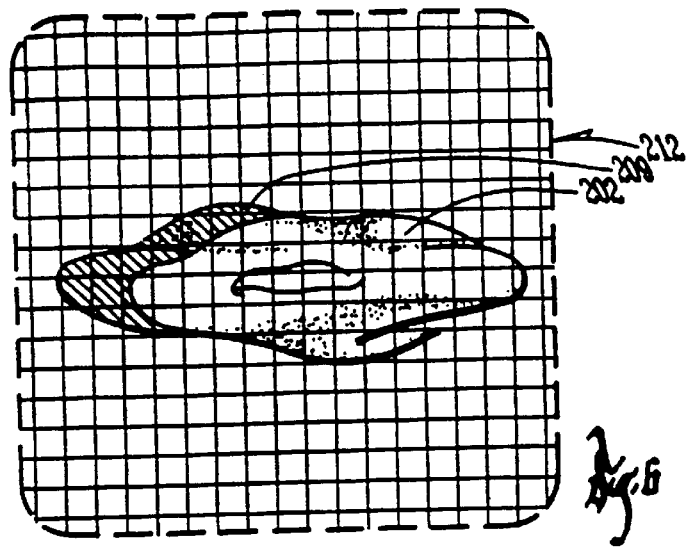
Figure 7:
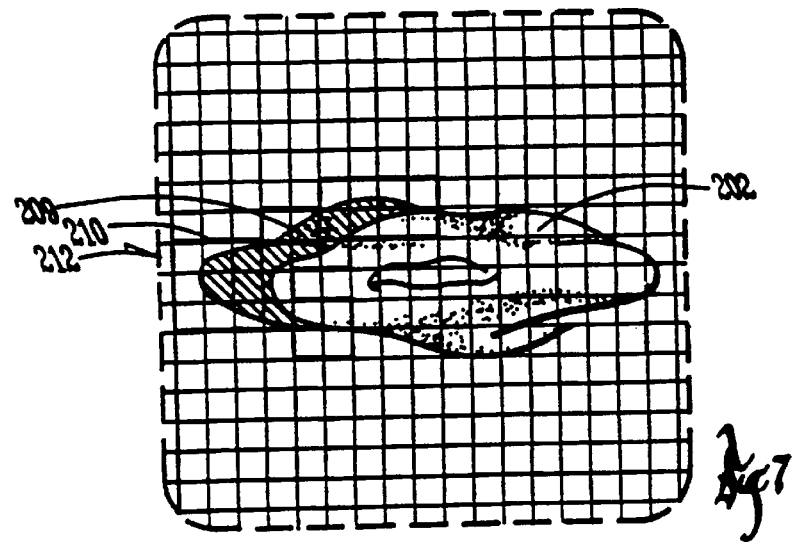
Figure 8:
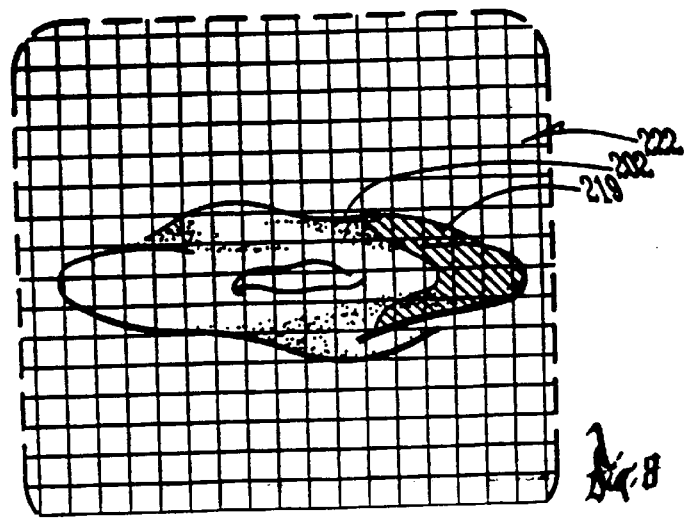
Figure 11:
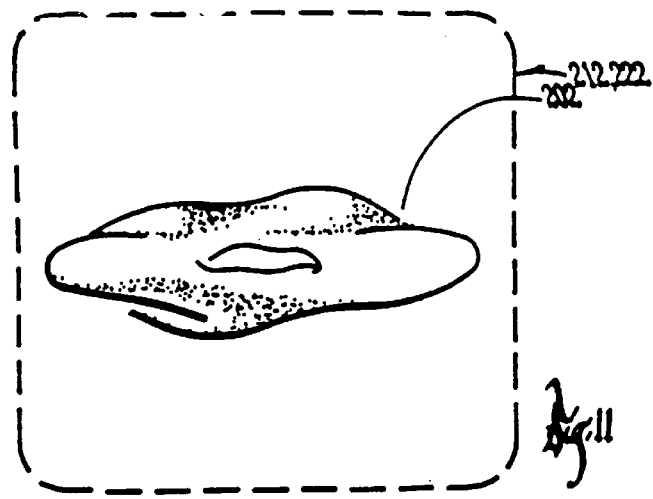
Figure 12:
FIGS. 12–14 are a series of example images produced and displayed in accordance with an embodiment of the present invention.
Figure 13:
Figure 14:

In the following description of preferred embodiments of the invention, particular reference will be made to methods and apparatus for optically imaging cervical tissue that is being analyzed for cancerous abnormalities. It will be appreciated by those skilled in the art that the present invention is not limited to such treatment, but can be equally applied to imaging of any mammalian tissue for the identification of cancerous and pre-cancerous abnormalities.

4.1. OVERVIEW-THE INVENTIVE COLPOSCOPY SYSTEM

Referring first to FIG. 1, the apparatus of the invention is generally designated by the numeral 10. Apparatus 10 includes a colposcope 20, a digital imaging means in the form of a digital camera 30, a frame capturing means in the form of a frame grabber 40, a digital processing means in the form of a computer 50, and computer peripherals 60.

Colposcope 20 includes a colposcope head 70, a light source 76, and control panel 78. The colposcope head 70 includes a pair of oculars 80, lens 81, a beam splitter 82, focusing assembly 83, video output 84, and camera mounting structure 86. Main lamp assembly 76 includes a conventional colposcope light 88, an optics fiber 90 operably attached at one end to control panel 78 and at the other end to lighting lens assembly 91. Lighting lens assembly 91 includes a mirror and lens (not shown) operable to illuminate an object for viewing through the colposcope head 70. Lighting lens assembly 91 is mounted to the colposcope head 70 as shown in FIG. 3.

As shown in FIGS. 21 and 22, the apparatus 10 of the present invention includes an extension arm assembly 72 and a stand assembly 74. The stand assembly preferably includes five side panels, indicated generally at 73 and an upper section 75. The side panels 73 of the stand assembly 74 define a housing (not shown) for storing the computer hardware and software of the present invention. The housing includes a door for permitting easy access to the computer hardware and software. Further, the lower end of the stand assembly 74 is configured with rollers 77 that permit easy and convenient movement of the mobile colposcope assembly 10. Extension arm assembly 72 includes articulated structure and is pivotally and swingably mounted at one end to colposcope head 70 and at its opposite end to the upper section 75 of the mobile stand assembly.

The video monitor 79 is mounted to the stand assembly in a fashion that permits both the doctor and the patient to view the digital colposcopic image. Preferably, the video monitor is rotatably and telescopically mounted on an upper section of the stand assembly. As shown, the monitor 79 is mounted on a shaft 81 that extends through an aperture of the first section of the extension arm. The shaft 81 is rotatably and extendably mounted in upper section the stand assembly. Preferably, the monitor is a flat screen panel, color monitor. The monitor is positionable to be viewed by the doctor to insure that the digital image is free of shadows and, if this is a second image of the cervix, is properly registered with a previous, archived image.

In a preferred embodiment, colposcope 20 provides a stereo vision, microscopic perspective view of cervical topology through the combination of a pair of optical paths a and b, as shown in FIG. 1. A third optical path is provided by beam splitter 82 placed in one optical path, for example optical path b, to split and direct the image along a third optical path c into the video output 84.

Control panel 78 includes housing 136, input port 138, power supply 140, delay logic system 142, and colposcope light 88.

Frame grabber 40 is designed as a personal computer peripheral card of conventional design and includes video input 148, control output 149, and data input/output 152. In the preferred embodiment, the data input/output bus is accomplished via an industry standard PCI bus as interfaced to a Pentium® personal computer. Referring to FIG. 17, a block diagram of a PIXCI™ frame grabber computer peripheral card is presented. The frame grabber imaging board includes a multiplexer 151, an automatic gain 152, a luminous A/D converter 153, a chrominance A/D converter 154, decoder 155, digital genlock/interperlate clock generation feature 156, a scale cropping temporal scaling feature 157, a PCI interface 158, and a trigger I/O 159. The frame grabber 40 in a preferred embodiment is an Epix Corporation, and is capable of grabbing any one frame of a continuous sequence of frames from video output generating frames at 30 frames per second. Frame grabber 40 also preferably includes a synchronize trigger feature, and memory buffers.

Computer 50 is of conventional personal computer design and has, in the preferred embodiment, the following processing features: a 166 Mhz Pentium micro processor, 32 Mbytes of RAM memory, hard drive disk storage capability, and an RGB color output capability. For the purposes of disclosing the invention, however, Computer 50 is disclosed in terms of a input data 160, mother board 162 (containing the Pentium or other microprocessor), printer output 164, monitor output 166, and bus 170 that is preferably a PCI bus, but may also be an ISA bus. It is understood, however, that computer 50 comprises all other features and functionalities that are well known to be associated with personal computers. Peripherals 60 include video monitor 167 and printer 168.

In the preferred embodiment, the colposcope 20 can be obtained from Cooper Surgical, 15 Forest Parkway, Shelton, Conn., and can be either model OZM-230 or OZM-310, which are models with magnification ranging from 2.8× up to 24×, working distance fields of view ranging between 98.5 mm and 5.6 mm and depths of field of either 230 mm or 310 mm and that include a variable zoom optics system. The main lamp for the Cooper Surgical colposcope used in the example is a 150 w, halogen fiber optics source with variable intensity. The optics system in the colposcopic head 70 includes a red-free green filter. The colposcope head may be adjusted to a height of between 37" to 57". As shown in FIG. 3, when used to conduct a pelvic examination the colposcope head 70 is oriented so that the lens is directed to the vaginal area making the vaginal cavity visible through oculars 80. The operation of a conventional colposcope 20, as used in an examination as shown in FIG. 3, is oriented such that an image of the entire cervix can be obtained.

Digital camera 30 is of conventional design, and in the preferred embodiment, is a Coopers Surgical brand HS4000 brand having a one-half inch CCD image sensor, CCD chip size of 4.6 mm. (H)×4.8 mm (V), picture elements: 768 (H) by 494 (V) or 752 (H) by 582 (V), a 2:1 interlaced scanning system, a 1.5 Lux/F 1.2 (3200 k) minimum illumination, 500 TV lines resolution, better than 45 db (AGC OFF) signal to noise ratio, a power supply DC 12 V/250 mA, a C/CS lens mount, dimensions: 50.5 (W)×50.5(H)×145(D) mn, wt=450 g. and has the following connectors: video-VMC or via 9 pin D-SUB plug; power-DC-JAK or via 9 pin D SUB plug; auto iris: 4 pin mini jack; and ext. sync-9 pin D-SUB plug.

Figure 15:
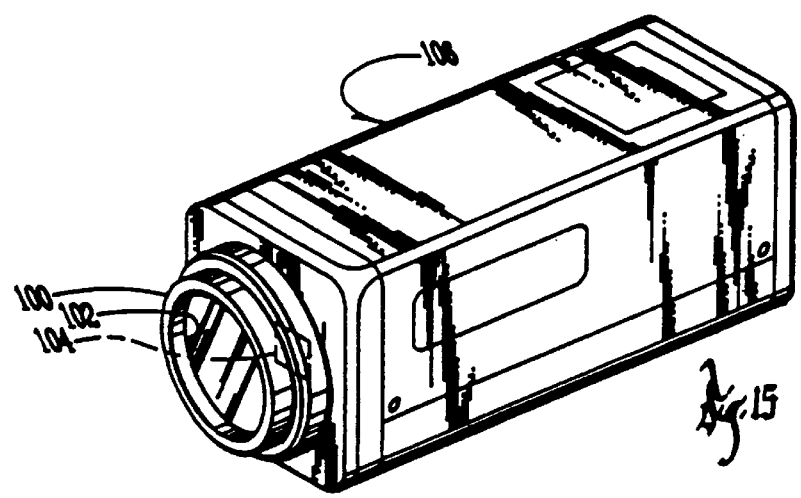
FIG. 15 is a perspective of a digital camera employed in the present invention.
Figure 16:
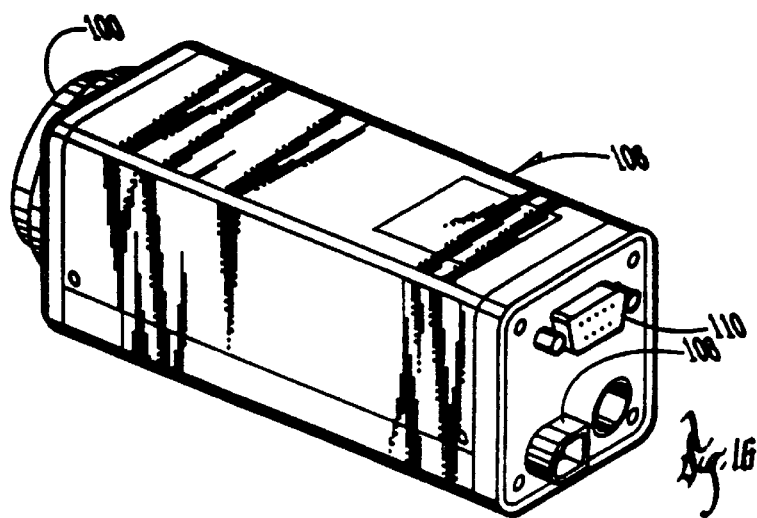
FIG. 16 is a perspective of a digital camera employed in the present invention.

Camera 30, as shown in FIGS. 15–16, includes lens mount 100, image sensor opening 102, CCD chip 104, camera housing 106, video output port 84, and camera input port 110. In the preferred embodiment, camera 30 employs a single CCD chip for image creation when processing. The invention, however, may be practiced with a camera making use of multiple CCD chips.

Digital camera 30 is adjustably secured to colposcopic head 70 by joining camera lens mount 100 of camera 30 to mount structure 86 of head 70. Camera 30 is mounted to head 70 in such an orientation so as to place CCD chip 104 into optical path c reflected from beam splitter 82 and is brought into proper focus by focus assembly 83. Camera video output 84 is supplied via line 180 to frame grabber input 148. Frame grabber control output 150 is connected to camera input 110 via line 182. Line 186 joins line 182 and provides a signal to relay logic control 142 via control panel input port 138.

4.2. CREATION OF DIGITAL IMAGES OF VAGINAL CAVITIES—THE TECHNIQUE

A general description of conventional techniques for the creation of digital images as employed by apparatus 10 will now be provided.

4.2.1 Creation of Digital Images Generally

Processes and equipment associated with the generation of digital images are well known in the art and are described in references such as Baxes, G. A., "*Digital Image Processing,*" John Wiley & Sons (1994) (ISBN 0-471-00949-0) Awcock, G. W. and Thomas, R., "*Applied Image Processing,*" McGraw-Hill, Inc. (1995) (ISBN 0-07 001470-1); Russ, J. C., "*The Image Processing Handbook,*" CRC Press (2nd Ed. 1995) (ISBN 0-8493-2516-1).

Non-digitized images, such as conventional photographs, are comprised of continuously varying shades and colors. The shades vary from light to dark and the colors vary from red, green, to blues.

A digital image is composed of discrete levels of gray tone ("brightness"), as opposed to the continuously varying tones associated with non-digitized conventional photographs. A digital image is created from a continuous tone image by dividing it up into individual points of brightness. (See FIG. 18) Each point of brightness is converted into a digital data value. The process of digitizing an image is called "sampling," and the process of converting each discrete sampled item into a digital value is call "quantization." The sampling process samples the intensity of the continuous-tone image at specific locations. The quantization process determines the digital brightness values of each sample ranging from black, to grays, to white. The quantized spacial sample is referred to as a picture element, or "pixel." The processes of sampling and quantization are collectively referred to as image digitization.

Figure 19:
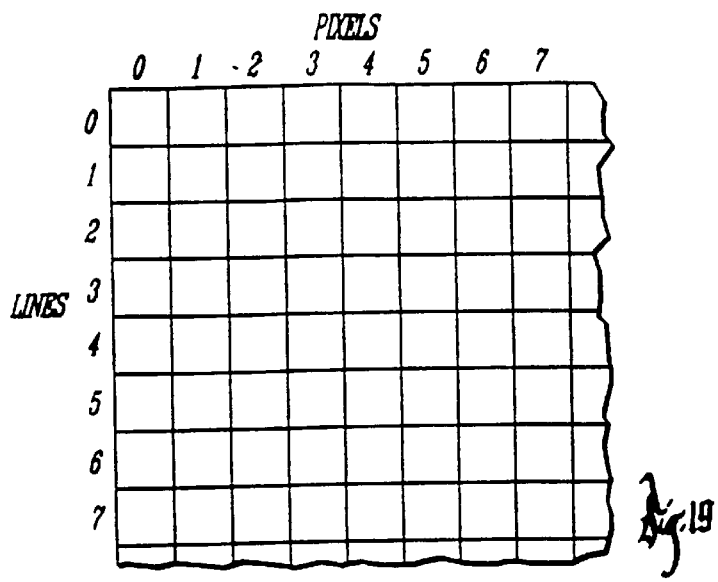
FIG. 19 is a representation of a pixel array.

Referring to FIG. 18, in image digitization, an image is generally sampled into a rectangular array of pixels 186. Each pixel has its own (x, y) coordinate that corresponds to its location within the rectangular array that comprises the image. Once sampled and quantized, each pixel will have generated an output quantity that is proportional to the input lighting intensity. Image resolution is thus a function of the number of pixels that make up the rectangular array and the capability of the digital image to resolve the elements, as closely as possible, to the original scene. The pixel arrays are traditionally orthogonal (Cartesian geometry) such as that shown in FIG. 18 and 19. Arrays, however, may also have an hexagonal configuration. See, e.g., Awcock, et al., "*Applied Image Processing,*" at 64.

With charge couple device technologies ("CCD"), it is possible to place more than 300,000 pixels in an area of less than one square centimeter. More specifically, there are 307,200 pixels in a conventional 640×480 array. Each pixel of a CCD functions as a detector of light intensity, and more specifically as a photo counter, as electrons are raised to the conduction band in an isolated well.

Figure 20:
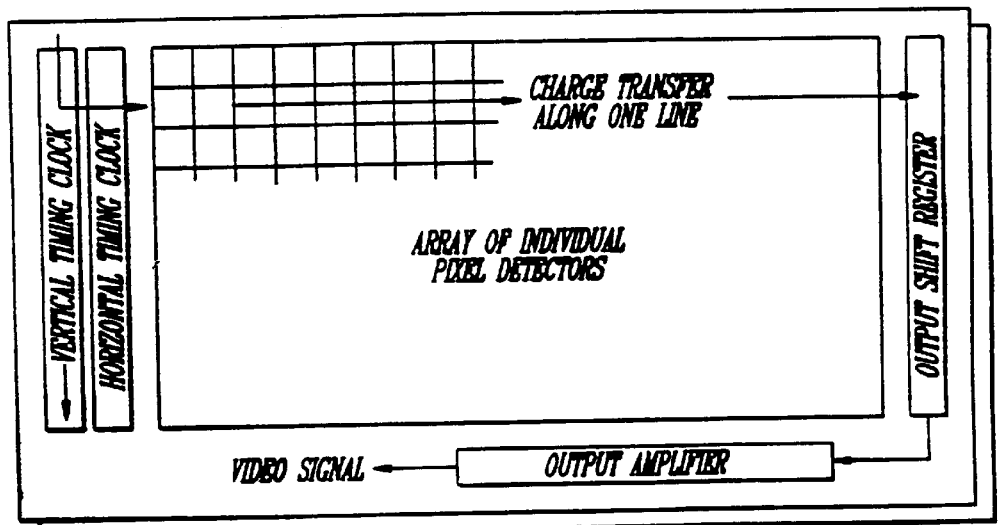
FIG. 20 is a representation of pixel charge transfer.

Referring to FIG. 20, a signal is read out from each line of detector pixels to produce an analog voltage. FIG. 20 shows a schematic diagram of a typical CCD camera chip. A vertical timing clock selects each line of pixel detectors in turn. Then a horizontal clock shifts the contents from each detector to its neighbor, causing the line to read out sequentially into a shift register and amplifier that produces an analog voltage as a function of time. Specific CCD array architectures include (a) parallel/serial; (b) interlined transfer; and (c) frame transfer.

The process previously described for the generation of digital images also applies to color images. In a single CCD chip comprised of a rectangular array of pixels capable of generating a color image, pixels in each line are constructed with filters such that every third pixel in each line detects red, blue, and green light. A single color CCD chip will be composed of detector pixels in repeating sequential groups of red, green, and blue detectors. Thus, if each detector has a gray-scale of $2^8$, it will create an analog output between 0 and 255 that is proportional to the red, green, or blue light intensity striking the particular detector. Further, as schematically shown in FIG. 23, each pixel consisting of a red, green, and blue detector are represented by a 24-bit word.

In digital imaging, a wide range of colors can be created by mixing red, blue, and green in various combinations, and are well developed in the art. See, e.g., Baxs, "*Digital Imaging Processing,*" at 53–56.

It will thus be appreciated that the processes described herein for monochrome digital imaging can be employed in color digital imaging by first converting the 24-bit color words in the pixel array rectangle into individual color intensity values. The conversion process applied in reverse is then used to recreate a color digital image using color intensity values.

4.2.1.1 Operation of Inventive Colposcope to Produce Digital Images of a Cervico-vaginal tissue Referring to FIGS. 1–4, colposcope 20 is positioned so that head 70 is oriented in the vaginal region to permit viewing into the vaginal cavity 196 through the vagina 198 into which a speculum 200 is inserted in the vagina 198 and is adjusted so that the cervico-vaginal tissue 202 will be in view. By viewing the cervix 202 through oculars 80, colposcope head 70 is aligned so that cervix 202 is centered on optical paths A and B (FIG. 1) and is adjusted so that the cervix 202 is viewed in its entirety. To assist with the proper alignment of colposcopic head 70, main lamp assembly 76 is switched on so that light 88 travels along optics fiber 90 and is redirected through lighting lens assembly 91. Assembly 91 is mounted to head 70 so that it illuminates objects in optical path c. Head 70 is typically located so that the cervix is about 300 mm from lens 81, in order to provide a convenient work, distance for the placement of colposcopic hand utensils such as biopsy punches. This distance may, of course, vary when different optical systems are selected for desired viewing characteristics and functionalities.

With the cervix 202 properly positioned within optical paths A and B of head 70, as shown in FIG. 1, beam splitter 82 can be employed to direct a split beam along optical path C and through camera opening 102 so that the image of cervix 202 will be directed upon CCD chip 104. Appropriate optics are selected and adjusted so that the image of the cervix is focused on CCD chip 104 to achieve the desired results. For example, it is typically preferable that the cervix 202 image comprise substantially the entire rectangular pixel array that comprises CCD chip 104.

Camera 30 is operable to generate a video image output of cervix 202 that comprises the generation an output at the rate of 30 image frames per second. It will be appreciated, however, that the invention can be practiced with video outputs generated at different rates.

The video output exits camera output port 106 and is directed to frame grabber video input port 148 via line 180. Frame grabber 40 is operable to asynchronously select any of the video images created by camera 30 and generate a image signal which exits the frame grabber 40 through data output port 152 and is sent to mother board 162 via bus 168. Mother board 162 of computer 50 is then operable to archive an image for any desirable purpose, including enhancement, documentation, archival, or transmission to other destinations. Computer 50 is further operable to reproduce a digital image of cervix 202 on monitor 167 or in hard copy by means of reproduction of image by printer 168.

4.3. ALTERNATIVES/OPTIONS

The included preferred embodiment is given by way of example only, and not by way of limitation to the invention, which is solely described by the claims herein. Variations obvious to one skilled in the art will be included within the invention defined by the claims.

4.3.1 Video Camera

The invention may also be practiced with a video camera that is mountable to the colposcope head 70 as a substitute for the digital camera 30, described above. The practice of the invention with a video camera in place of a digital camera would only require appropriate mounting fixtures for securing the video camera to the colposcope head 70 with appropriate electrical connections so that a video camera would serve the functions and objectives of the invention as described above.

4.3.2 Other Light Sources

With respect to illumination of an object, various light sources (frequencies and light intensities) may be employed to achieve a wide variety desired effects.

4.3.3 Computer

Computer 50, and particularly user interface circuitry, is designed and configured to permit enhancement of digital images created with apparatus 10 for screening and diagnostic purposes. Conventional digital imaging enhancement techniques are used to facilitate visualization of tissue texture, tissue and lesion borderlines and tissue vascularity, all important components of cancer screening and diagnosis. Specific enhancement techniques include, but are not limited, to those disclosed in: Cristoforoni, M.D., Gerbaldo, M.D., Perino, M.D., and Capitanio, M.D., *Computerized Colposcopy: Results of a Pilot study and Analysis of its Clinical Relevance*, Obstetrics and Gynecology, Vol. 85, No. 6 (June 1995); Contini, M.D., Zobbi, M.D., Pasquinucci, M.D., *Colposcopy and Computer Graphics: A New Method?*, AM. J. Obstet. Gynecol. (1989); Shafi, Dunn, Chenoy, Buxton, Williams, Luesley, *Digital Imaging Colposcopy, Image Analysis and Quantification of the Colposcopic Image*, British Journal of Obstetrics and Gynecology, Vol. 101, pp. 234–38 (March 1994); Mikhail, M.D., Merkatz, M.D., and Romney, M.D., *Clinical Usefulness of Computerized Colposcopy: Image Analysis and Conservative Management of Mild Dysplasia*, Obstetrics & Gynecology, Vol. 80, No. 1 (July 1992), all teaching of which are hereby incorporated by reference.

I claim:

1. A self-contained cervical cancer detection apparatus for digital imaging of a cervico-vaginal tissue, comprising:
   a. an assembly having an extension arm assembly and a stand assembly,
   b. a digital-imaging colposcope mounted to the extension arm assembly, said digital imaging colposcope having a colposcopic head, a digital camera for producing more than one digital image of the cervico-vaginal tissue, and a frame grabber for selecting one of the more than one digital images of the digital images,
   c. digital processing means operable to enhance a digital image, the digital processing means being housed in the stand assembly, and
   d. a video monitor mounted to the stand assembly whereby a series of digital images of the cervico-vaginal image may be viewed by an operator of the cervical cancer detection apparatus and an optimum image created through the digital processing means while viewing the enhanced image on the video monitor.

2. The apparatus according to claim 1, wherein the digital processing means comprises a computer software and hardware system.

3. The apparatus according to claim 1, wherein the video monitor is a flat panel video monitor.

4. The apparatus according to claim 1, wherein the video monitor is swingably mounted to the stand assembly for displaying the digital image.

5. The apparatus according to claim 1, wherein the video monitor is telescopically mounted to the base of the assembly for permitting the video monitor to be adjusted to a proper height for viewing by a user.

6. The apparatus according to claim 1 wherein the apparatus is mobile.

7. The apparatus according to claim 6, wherein the stand assembly includes rollers to permit the apparatus to be mobile.

8. The apparatus according to claim 1, wherein the digital-imaging colposcope comprises a digital camera operably coupled to a colposcope including a beam splitter.

9. The apparatus according to claim 3, wherein the digital camera is configured to create color digital images.

* * * * *